(12) United States Patent
Berezkin et al.

(10) Patent No.: US 7,452,525 B1
(45) Date of Patent: Nov. 18, 2008

(54) POLYURETHANE DISPERSIONS BASED ON POLYCARBONATE POLYOLS AND SUITABLE FOR USE IN PERSONAL CARE PRODUCTS

(76) Inventors: Yuliya Berezkin, 1567 Tiffany Dr., Pittsburgh, PA (US) 15241; Peter D. Schmitt, 428 Sherwood Dr., Beaver, PA (US) 15009-1062; Serkan Unal, 1510 Shady Ave., Pittsburgh, PA (US) 15217

( * ) Notice: Subject to any disclaimer, the term of this patent is extended or adjusted under 35 U.S.C. 154(b) by 0 days.

(21) Appl. No.: 11/890,979

(22) Filed: Aug. 8, 2007

(51) Int. Cl.
*A61K 8/00* (2006.01)
*A61K 8/18* (2006.01)
*A61K 9/14* (2006.01)
*A61K 8/72* (2006.01)
*A61K 31/74* (2006.01)
*A61Q 17/04* (2006.01)
*A61Q 5/00* (2006.01)
*A61Q 7/00* (2006.01)

(52) U.S. Cl. .................. 424/59; 424/486; 424/70.11; 424/78.03

(58) Field of Classification Search .................. None
See application file for complete search history.

(56) References Cited

U.S. PATENT DOCUMENTS

| 5,626,840 | A | 5/1997 | Thomaides et al. ...... 424/70.11 |
| 5,643,581 | A | 7/1997 | Mougin et al. ............... 424/401 |
| 5,968,494 | A | 10/1999 | Kukkala et al. ............ 424/70.1 |
| 6,007,793 | A | 12/1999 | Bhatt et al. .................... 424/47 |
| 6,106,813 | A | 8/2000 | Mondet et al. ................. 424/61 |
| 6,277,386 | B1 | 8/2001 | Kim et al. .................... 424/401 |
| 6,291,580 | B1 | 9/2001 | Kukkala et al. ............. 524/840 |
| 6,368,583 | B1 | 4/2002 | Kim et al. .............. 424/70.122 |
| 6,407,158 | B1 | 6/2002 | Kim et al. .................... 524/539 |
| 6,517,821 | B1 | 2/2003 | Rollat et al. .............. 424/70.11 |
| 6,524,564 | B1 | 2/2003 | Kim et al. ................. 424/70.12 |
| 6,613,314 | B1 | 9/2003 | Rollat et al. ................ 424/70.1 |
| 6,692,729 | B1 | 2/2004 | Asaoka et al. ............. 424/70.1 |
| 6,897,281 | B2 | 5/2005 | Lubnin et al. ................. 528/44 |
| 2004/0197293 | A1 | 10/2004 | Mougin ................... 424/70.17 |

*Primary Examiner*—Johann Richter
*Assistant Examiner*—Luke E Karpinski
(74) *Attorney, Agent, or Firm*—Noland J. Cheung; Robert S. Klemz

(57) ABSTRACT

The invention relates to a process for preparing an aqueous polyurethane dispersion suitable for use in personal care products, wherein the polyurethane is based on one or more polycarbonate polyols.

15 Claims, No Drawings

POLYURETHANE DISPERSIONS BASED ON POLYCARBONATE POLYOLS AND SUITABLE FOR USE IN PERSONAL CARE PRODUCTS

BACKGROUND OF THE INVENTION

The invention relates to aqueous polyurethane dispersions, to a process for preparing them and to their use in cosmetic applications such as hair fixatives.

Polyurethane dispersions have recently been incorporated into cosmetic products, such as hair fixatives, suntan lotions, etc., offering several advantages over conventional technologies such as acrylics and acryl amide copolymers, polyvinyl pyrrolidone, and PVP/VA copolymers. Such advantages include water compatibility, ease of formulating low VOC sprays, water resistance and excellent film forming ability. Specifically in hair care products, polyurethane dispersions provide great setting effect without sticky feel, excellent style retention owing to the polymer's elastic memory, natural look and feel. All these attributes are highly valuable to the consumer. Commercial polyurethane dispersions designed as hair fixatives and hair styling polymers generally exhibit good high humidity curl retention, style retention, good feel and shine. However, their lack of adhesion to hair is demonstrated by extensive flakiness on hair after combing. This creates a significant aesthetic problem for consumers.

The challenge of designing a hair fixative polymer consists of achieving a balance between often conflicting requirements: the polymer should be hydrophobic enough to provide curl retention even under humid conditions, while it should remain sufficiently hydrophilic in order to be removable from hair by washing with water. Also, the polymer has to possess an optimum combination of glass transition temperature, flexibility and molecular weight to provide setting strength, elasticity, adhesion to hair and soft feel.

U.S. Pat. No. 5,626,840 discloses hair fixatives based on polyurethane dispersions that are prepared utilizing 2,2-hydroxymethyl-substituted carboxylic acid. It illustrates how to achieve good humidity resistance and spray characteristics using water soluble or dispersable polyurethanes. The examples demonstrate the efficacy of the polymer only in aerosol spray formulations containing alcohol. This is detrimental for both the environment and the health of the hair. Finally, the invention utilizes a range of dimethylol propionic acid (DMPA) of 0.35-2.25 meq of COOH per gram of polyurethane in the polyurethane dispersion that must be observed in order for the dispersion to be effective.

However, the disclosure does not teach how to avoid the common problem of the polymer's flakiness on hair by achieving good adhesion to hair. Moreover, it does not teach how to attain style retention, e.g. elastic behavior of the polymer. Finally, a lower amount of acid should preferably be used, while still achieving curl retention and washability, as the acid tends to accelerate the breakdown of the polymer.

U.S. Pat. No. 6,613,314 discloses reshapeable hair compositions that utilize polyurethane dispersions. During preparation of the polyurethane, an isocyanate-functional prepolymer is formed. The prepolymer incorporates at least one polyactive hydrogen compound that is soluble in the medium of dispersion. Preferably, sulfonated compounds are utilized. The sulfonic group is incorporated into the prepolymer, rather than via the urea segment.

U.S. Pat. No. 6,106,813 discloses polyester polyurethanes that are suitable in cosmetic applications. It discloses a new family of polyester polyurethanes that possess not only good film-forming properties, but also impart great rigidity and excellent resistance to removal by water and detergents. With regard to the hair styling/hair fixative applications, the examples in the patent demonstrate the use of the invention only in hair style shaping lotions, claiming good shape retention.

However, the reference does not mention adhesion to hair or how to achieve excellent humidity resistance with good removability by water. It also does not mention important attributes of hair styling/hair fixative polymers, such as natural feel and luster on hair.

Thus, the purpose of present invention was to provide a polymer composition which would improve adhesion to hair and also demonstrate excellent curl and style retention, natural feel and look.

The present invention provides a composition that demonstrates excellent adhesion to hair. In comparison to commercially available hair fixative polyurethane dispersions, the composition of the present invention impart significantly less or no flaking at all. In addition, it provides improved humidity retention, higher luster and natural feel in comparison to the above-mentioned polyurethane dispersions.

SUMMARY OF THE INVENTION

The present invention relates to a process for preparing an aqueous polyurethane dispersion suitable for use in personal care products, comprising:

1) preparing a prepolymer according to the formula:

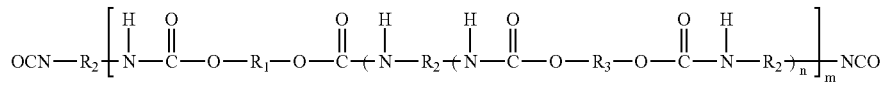

wherein
$R_1$ represents a bivalent radical of a polycarbonate polyol,
$R_2$ represents a radical of an aliphatic or cycloaliphatic polyisocyanate,
$R_3$ represents a radical of a low molecular weight diol, optionally substituted with ionic groups,
n is from 1 to 5, and
m is >1;
by reacting:
  1a) at least one polycarbonate polyol,
  1b) one or more aliphatic or cycloaliphatic polyisocyanates, and
  1c) at least one low molecular weight diol optionally substituted with ionic groups;
2) reacting the prepolymer with at least one monohydroxyl-functional polyalkylene oxide with a number average molecular weight of less than about 3,000;
3) chain-extending the prepolymer with
  3a) at least one chain extender according to the formula:

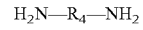

wherein $R_4$ represents an alkylene or alkylene oxide radical not substituted with ionic or potentially ionic groups, and 3b) optionally at least one chain extender according to the formula:

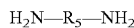
$$H_2N-R_5-NH_2$$

wherein $R_5$ represents an alkylene radical substituted with ionic or potentially ionic groups, in the presence of an organic solvent to form a polyurethane;

4) dispersing the polyurethane in water; and 5) removing the organic solvent, resulting in an aqueous polyurethane dispersion;

wherein the radical of the monohydroxyl-functional polyalkylene oxide constitutes between about 0.1 wt. % to about 5 wt. % of the polyurethane.

DETAILED DESCRIPTION OF THE PREFERRED EMBODIMENTS

As used herein and in the following claims, unless indicated otherwise, the term "molecular weight" shall be interpreted to mean number average molecular weight.

Suitable polycarbonate polyols for providing the bivalent radical $R_1$ are polycarbonate polyols having at least two hydroxyl groups and having number average molecular weights of from about 700 to about 16,000, and preferably from about 750 to about 5000.

Polycarbonates containing hydroxyl groups include those known per se such as the products obtained from the reaction of diols such as propanediol-(1,3), butanediol-(1,4) and/or hexanediol-(1,6), diethylene glycol, bisphenol-A, triethylene glycol or tetraethylene glycol with diarylcarbonates, e.g. diphenylcarbonate, dimethylcarbonate, diethyleneglycol carbonate or phosgene.

Suitable polyisocyanates for providing the hydrocarbon radical $R_2$ include organic diisocyanates having a molecular weight of from about 112 to 1,000, and preferably from about 140 to 400. Preferred diisocyanates are those represented by the general formula $R_2(NCO)_2$ indicated above in which $R_2$ represents a bivalent aliphatic hydrocarbon group having from 4 to 18 carbon atoms, a bivalent cycloaliphatic hydrocarbon group having from 5 to 15 carbon atoms, a bivalent araliphatic hydrocarbon group having from 7 to 15 carbon atoms or a bivalent aromatic hydrocarbon group having 6-15 carbon atoms. Examples of the organic diisocyanates which are suitable include tetramethylene diisocyanate, 1,6-hexamethylene diisocyanate, dodecamethylene diisocyanate, cyclohexane-1,3- and -1,4-diisocyanate, 1-isocyanato-3-isocyanatomethyl-3,5,5-trimethylcyclohexane (isophorone diisocyanate or IPDI), bis-(4-isocyanatocyclohexyl)-methane, 1,3- and 1,4-bis(isocyanatomethyl)-cyclohexane, bis-(4-isocyanato-3-methyl-cyclohexyl)-methane, isomers of toluene diisocyanate (TDI) such as 2,4-diisocyanatotoluene, 2,6-diisocyanatotoluene, mixtures of these isomers, hydrogenated TDI, 4,4'-diisocyanato diphenyl methane and its isomeric mixtures with 2,4'- and optionally 2,2'-diisocyanato diphenylmethane, and 1,5-diisocyanato naphthalene. Mixtures of diisocyanates can, of course, be used. Preferred diisocyanates are aliphatic and cycloaliphatic diisocyanates. Particularly preferred are 1,6-hexamethylene diisocyanate and isophorone diisocyanate.

The low molecular weight diols usually result in a stiffening of the polymer chain, when they are used. By "low molecular weight diols" it is meant diols having a molecular weight from about 62 to 700, preferably 62 to 200. At least one of the low molecular weight diols contains ionic or potentially ionic groups. Suitable lower molecular weight diols containing ionic or potentially ionic groups are those disclosed in U.S. Pat. No. 3,412,054. Preferred compounds include dimethylol butanoic acid (DMBA), dimethylol propionic acid (DMBA) and carboxyl-containing caprolactone polyester diol. The lower molecular weight diols containing ionic or potentially ionic groups are used in an amount such that <0.30 meq of COOH per gram of polyurethane in the polyurethane dispersion are present.

Other low molecular weight diols not containing ionic or potentially ionic groups may optionally be used. They may contain aliphatic, alicyclic or aromatic groups. Preferred compounds contain only aliphatic groups. The low molecular weight diols having up to about 20 carbon atoms per molecule include ethylene glycol, diethylene glycol, propane 1,2-diol, propane 1,3-diol, butane 1,4-diol, butylene 1,3-glycol, neopentyl glycol, butyl ethyl propane diol, cyclohexane diol, 1,4-cyclohexane dimethanol, hexane 1,6-diol, bisphenol A (2,2-bis(4-hydroxy-phenyl)propane), hydrogenated bisphenol A (2,2-bis(4-hydroxycyclohexyl)-propane), and mixtures thereof.

The monohydroxyl-functional polyalkylene oxide compounds suitable for use in the present invention include any monohydroxyl-functional polyether with a number average molecular weight of less than about 3,000, preferably from 300 to 3,000, based on ethylene oxide or propylene oxide or both. Suitable compounds include Desmophen® LB-25, an ethylene oxide/polyethylene oxide monol available from Bayer MaterialScience, Pittsburgh, Pa., the CARBOWAX SENTRY line of methoxypolyethylene glycols available from Dow Chemical Company, Midland, Mich., as well as the UCON LB Fluids and UCON 50-HB Fluids, also available from Dow Chemical Company. The monohydroxyl-functional compounds are used in an amount such that the polyalkylene oxide radicals incorporated into the prepolymer via the urethane segment constitute between about 0.1 wt. % to about 5 wt. % of the polyurethane.

The prepolymer may be chain extended using at least one, optionally two classes of chain extenders. First, compounds having the formula:

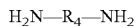
$$H_2N-R_4-NH_2$$

wherein $R_4$ represents an alkylene or alkylene oxide radical not substituted with ionic or potentially ionic groups are used. Alkylene diamines include hydrazine, ethylenediamine, propylenediamine, 1,4-butylenediamine and piperazine, 2-methyl-1,5-pentanediamine (Dytek A from DuPont), hexane diamine, isophorone diamine, and 4,4-methylenedi(cyclohexylamine). The alkylene oxide diamines include 4,7,10-trioxa-1,13-tridecanediamine (also known as diproplyamine diethyleneclycol or DPA-DEG or Ancamine® 1922A available from Air Products, Allentown, Pa.) and the ANCAMINE series ether amines available from Air Products, including dipropylamine propyleneglycol, dipropylamine dipropyleneglycol, dipropylamine tripropyleneglycol, dipropylamine poly(propylene glycol), dipropylamine ethyleneglycol, dipropylamine poly(ethylene glycol), dipropylamine 1,3-propane diol, dipropylamine 2-methyl-1,3-propane diol, dipropylamine 1,4-butane diol, dipropylamine 1,3-butane diol, dipropylamine 1,6-hexane diol and dipropylamine cyclohexane-1,4-dimethanol. Mixtures of the listed diamines may also be used. The first class of chain extenders may have a molecular weight from about 100 to 1500, preferably from about 170 to 1000.

The optional second class of chain extenders is compounds having the formula:

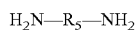

wherein $R_5$ represents an alkylene radical substituted with ionic or potentially ionic groups. Such compounds have an ionic or potentially ionic group and two groups that are reactive with isocyanate groups. Such compounds contain two isocyanate-reactive groups and an ionic group or group capable of forming an ionic group. The ionic group or potentially ionic group can be selected from the group consisting of ternary or quaternary ammonium groups, groups convertible into such a group, a carboxyl group, a carboxylate group, a sulfonic acid group and a sulfonate group. The at least partial conversion of the groups convertible into salt groups of the type mentioned may take place before or during the mixing with water. Specific compounds include diaminosulfonates, such as for example the sodium salt of N-(2-aminoethyl)-2-aminoethane sulfonic acid or the sodium salt of N-(2-aminoethyl)-2-aminopropionic acid. The second class of chain extenders may have a molecular weight from about 32 to 600, preferably from about 32 to 200.

The polyurethane according to the invention may also include compounds which are situated in each case at the chain ends and terminate said chains (chain terminators). These chain terminators can be derived from compounds having the formula:

wherein $R_6$ is an H atom or alkylene radical optionally having a hydroxyl end and $R_7$ is alkylene radical optionally having a hydroxyl end. Suitable compounds include compounds such as monoamiines, particularly monosecondary amines, or monoalcohols. Examples include: methylamine, ethylamine, propylamine, butylamine, octylamine, laurylamine, stearylamine, isononyloxy-propylamine, dimethylamine, diethylamine, dipropylamine, dibutylamine, N-methylamino-propylamine, diethyl(methyl)aminopropylamine, morpholine, piperidine, diethanolamine and suitable substituted derivatives thereof, amide amines of diprimary amines and monocarboxylic acids, monoketimes of diprimary amines, primary/tertiary amines such as N,N-dimethylaminopropylamine and the like. Also suitable are chain terminating alcohols such as, $C_1$-$C_{10}$ or higher alcohols including, methanol, butanol, hexanol, 2-ethylhexyl alcohol, isodecyl alcohol, and the like and even mixtures thereof, as well as aminoalcohols such as aminomethylpropanol (AMP). The chain terminators may have a molecular weight from about 31 to 600, preferably from about 31 to 200.

In one embodiment of the invention, diethylene glycol is incorporated into the polyurethane dispersion either as the low molecular weight diol, or as part of the non-ionic chain extender through the use of dipropylamine-diethyleneglycol ("DPA-DEG"). If the diethylene glycol is used as the low molecular weight diol, then preferably the DPA-DEG is not used as the non-ionic chain extender. Likewise, if the DPA-DEG is used as the non-ionic chain extender, then diethylene glycol is preferably not used as the low molecular weight diol. The use of the diethylene glycol or DPA-DEG is especially desirable when the polyurethane dispersion is incorporated into a hair fixative, as the diethylene glycol significantly increases the adhesion to hair.

The present invention also relates to a process for the production of a polyurethane dispersion suitable for use in personal care products, comprising a) reacting in a first step at least the polycarbonate polyol and the diisocyanate to form the prepolymer A), then b) dissolving in a second step the prepolymer in an organic solvent, c) reacting in a third step the isocyanate-containing prepolymer solution with the two classes of chain extenders and optionally, the chain terminator, d) forming, in a fourth step, the dispersion by addition of water, and e) removing in a fifth step the organic solvent.

Free sulfonic acid groups and carboxylic acid groups incorporated are neutralized between the second and third steps or between the third and fourth steps. Suitable neutralizing agents included are the primary, secondary or tertiary amines. Of these the trialkyl-substituted tertiary amines are preferred. Examples of these amines are trimethyl amine, triethyl amine, triisopropyl amine, tributyl amine, N,N-dimethyl-cyclohexyl amine, N,N-dimethylstearyl amine, N,N-dimethyl-aniline, N-methylmorpholine, N-ethylmorpholine, N-methylpiperazine, N-methylpyrrolidine, N-methylpiperidine, N,N-dimethyl-ethanol amine, N,N-diethyl-ethanol amine, triethanolamine, N-methyldiethanol amine, dimethylaminopropanol, 2-methoxyethyldimethyl amine, N-hydroxyethyl-piperazine, 2-(2-dimethylaminoethoxy)-ethanol and 5-diethylamino-2-pentanone. The most preferred tertiary amines are those which do not contain active hydrogen(s) as determined by the Zerewitinoff test since they are capable of reacting with the isocyanate groups of the prepolymers which can cause gelation, the formation of insoluble particles or chain termination.

The polyurethane dispersions according to the invention can be produced by the so-called acetone process. In the acetone process the synthesis of the aqueous preparations of polyurethane on which the dispersions according to the invention are based is performed in a multistage process.

In a first stage a prepolymer containing isocyanate groups is synthesized from the polycarbonate polyol, the diisocyanate and the low molecular weight diol. The amounts of the individual components are calculated in such a way that the isocyanate content of the prepolymer is between 1.4 and 5.0 wt. %, preferably between 2.0 and 4.5 wt. %, and particularly preferably between 2.6 and 4.0 wt. %. The low molecular weight diol is present in an amount from 0 to 80 eq. % based on the amount of NCO equivalents, preferably from 0 to 10 eq. %.

The resulting prepolymer has a structure of:

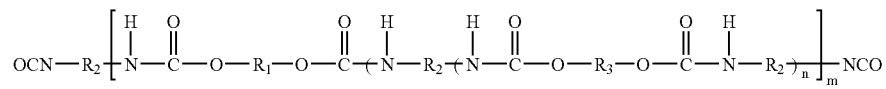

wherein
- R₁ represents a bivalent radical of a polycarbonate polyol,
- R₂ represents a hydrocarbon radical of an aliphatic or cycloaliphatic polyisocyanate,
- R₃ represents a radical of a low molecular weight diol, optionally substituted with ionic groups,
- n is <5, and
- m is >1.

Preferably, n is from 1 to 3, and m is from 1 to 5.

The prepolymer is then reacted with the monohydroxyl-functional polyalkylene oxide with a number average molecular weight of less than about 3,000.

In a second stage the prepolymer produced in stage 1 is dissolved in an organic, at least partially water-miscible, solvent containing no isocyanate-reactive groups. The preferred solvent is acetone. Other solvents, such as, for example, 2-butanone, tetrahydrofuran or dioxan or mixtures of these solvents can also be used, however. The quantities of solvent to be used must be calculated in such a way that a solids content of 25 to 60 wt. %, preferably 30 to 50 wt. %, particularly preferably 35 to 45 wt. %, is obtained.

In a third stage the isocyanate-containing prepolymer solution is reacted with mixtures of the amino-functional chain extenders and, optionally, chain terminator, to form the high-molecular weight polyurethane. Sufficient amounts of the chain extenders and chain terminator are used such that the calculated number-average molecular weight (Mn) of the resulting polyurethane is between 10,000 and 100,000 daltons, preferably between 10,000 and 50,000 daltons. The ionic and non-ionic chain extenders are present in an amount from 15 to 98 eq. %, preferably 35 to 80 eq. % total, based on the residual amount of NCO equivalents present in the prepolymer. The chain terminator is present in an amount from 0 to 35 eq. %, preferably from 10 to 20 eq. %, based on the residual amount of NCO equivalents present in the prepolymer.

In a fourth stage the high-molecular weight polyurethane is dispersed in the form of a fine-particle dispersion by addition of water to the solution or solution to the water.

In a fifth stage the organic solvent is partially or wholly removed by distillation, optionally under reduced pressure. The amount of water in stage four is calculated in such a way that the aqueous polyurethane dispersions according to the invention display a solids content of 20 to 60 wt. %, preferably 28 to 42 wt. %.

The polyurethane dispersions of the present invention are suitable for use in personal care products. Preferably, they are used in non-aerosol hair fixatives. Such hair fixatives are easily prepared by the addition of water or ethanol to the dispersion. Likewise, the dispersions may be used in the preparation of other personal care products such as suntan lotions, skin care products, lipstick, mascara and deodorants, by the addition of components well known to those of ordinary skill in the art.

EXAMPLES

Products Used in the Examples

Desmophen® C-2200 (hexane diol-based polycarbonate, M/wt. 2000, OH No. 56; Bayer MaterialScience LLC, Pittsburgh, Pa.).

Desmodur® W (Dicyclohexylmethane-4,4'-diisocyanate, NCO content 31.8%, Bayer MaterialScience LLC, Pittsburgh, Pa.).

Desmodur® I (Isophorone diisocyanate, NCO content 37.5%, Bayer MaterialScience LLC, Pittsburgh, Pa.).

Desmophen® LB-25 (Ethylene oxide/Polyethlyene oxide monol, M/wt. 2220, Bayer MaterialScience LLC, Pittsburgh, Pa.).

Acclaim® 4200 (Propylene oxide based polyether diol, M/wt. 2,000, Bayer MaterialScience LLC, Pittsburgh, Pa.).

PPG 425 (Propylene oxide based polyether diol, M/wt. 425, Bayer MaterialScience LLC, Pittsburgh, Pa.).

Ancamine® 1922A (dipropylamine-diethyleneglycol, Air Products, Allentown, Pa.).

Kathon®LX (biocide, Rohm & Haas, Philadelphia, Pa.).

Microcare® MTG (biocide, Thor Specialties (UK) Ltd., Cheshire, UK).

Example 1

Composition According to the Invention 25.74 g of Desmophen® C-2200, 0.18 g neopentyl glycol, and 0.62 g of DMBA were mixed together in the flask at 75° C. to obtain a homogeneous mixture. 4.31 g of Desmodur® W and 3.65 g of Desmodur® I were added into the flask at 70° C. Reaction proceeded at 95° C. until actual NCO content became lower or equal to theoretical NCO. Then 0.7 g of Desmophen® LB-25 was added and reacted until actual NCO became constant. Prepolymer was cooled to 60° C., and 60 g acetone was charged into the reaction flask. The clear prepolymer solution was mixed for 15 min while cooling to 40° C. 0.43 g of triethylamine was added into the prepolymer solution at 40° C. and mixed for 10 min. Chain extension step took place next at 40° C. with the addition of 2.65 g of Ancamine® 1922A in 15 g of distilled water. After 15 min, 61.34 g of distilled water was added at room temperature into the prepolymer under 600 rpm agitation. Extra water was added as the dispersion became too viscous. The distillation of the acetone followed the dispersion stage. Upon completion of the distillation, 0.38 g of Microcare® MTG was added.

Examples 2-5 were prepared using the same procedure as Example 1.

Non-aerosol hair fixative formulations were prepared utilizing deionized water and the polyurethane dispersions according to the invention. The formulations were 4 parts polyurethane dispersion active resin solids by the mixing of 10 parts polyurethane dispersion and 90 parts water. The non-aerosol spray formulations (20 ml) containing 3% active resin solids were prepared as following: ((3/% solids PUD)× 20 ml)/100=X g of PUD dissolved in (20-X) g of water.

Curl retention testing was performed in accordance with the test methods detailed in U.S. Pat. No. 5,626,840. Spray bottles with fine mist were used for application. The sample hair used was Yaki brown hair, 8 in., color 4. The Curl Retention test was performed as follows. The hair was cut into swatches of ~2 g each and bound together at one end. Each swatch was washed in 10% solution of clarifying shampoo for 30 seconds and rinsed in warm tap water. The hair on each swatch was cut into 6 in length from secured end. Then the hair was wetted again and combed, and the excess water was squeezed out. The hair swatches were rolled and secured onto ½ in diameter rollers and dried at 49° C. for approximately one hour. The dried hair was removed from the roller and the resulting curl was suspended by the bound end. The curl height was measured for each swatch.

Each curl was sprayed uniformly with 4 sprays per side. The curl was placed in an aluminum pan and placed in a 49° C. oven for about 30 minutes to dry. The dried curl was then resuspended, and the curl length was measured for time 0 minutes, and set into Thermotron at 22° C., 95% R.H. The curl height was measured after 24 hours.

Curl retention was calculated as follows:

$$\% \text{ Curl Retention} = \frac{L-L'}{L-L°} \times 100$$

where L is length of hair fully extended, 6 in.

L° is length of curl before spray and exposure, and

L' is length of curl after spray and exposure.

Style retention was evaluated as follows: after 24 hours exposure to high humidity, the curl was combed 10 times. The style retention was judged based on the curl's ability to retain its initial shape and length. In most cases, the curl remained unaffected by combing.

Feel was evaluated as follows: untreated hair and hair and treated with PUD were subjected to a panel of 10 judges. Panelists were asked to rank the feel from 1-5, with 1 being the most natural soft feel with no revealing presence of the polymer.

Adhesion to hair was evaluated by running a comb through the treated hair, and visually observing the comb and the hair for flakes and residue.

|  | Ex. 1 | Ex. 2 | Ex. 3 | Ex. 4 | Ex. 5 |
|---|---|---|---|---|---|
| Component |  |  |  |  |  |
| Desmophen ® C 2200 | 25.74 | 28.19 | 19.23 | 19.25 | 26.89 |
| Acclaim ® 4200 | 0 | 0 | 9.43 | 8.13 | 0 |
| PPG 425 | 0 | 0 | 0.73 | 0.63 | 0 |
| Neopentyl glycol | 0.18 | 0 | 0 | 0 | 0.35 |
| Desmophen ® LB-25 | 0.70 | 0.77 | 0.77 | 0.66 | 1.49 |
| Dimethylol propanoic acid | 0 | 0 | 0 | 0 | 0.97 |
| Dimethylol butanoic acid | 0.62 | 0.97 | 0.89 | 0.81 | 0 |
| Desmodur ® W | 4.31 | 4.72 | 6.80 | 0 | 8.4 |
| Desmodur ® I | 3.65 | 4.00 | 1.54 | 6.40 | 1.39 |
| Triethylamine | 0.43 | 0.66 | 0.61 | 0.55 | 0.72 |
| Diethanolamine | 0 | 0 | 0 | 0 | 0 |
| Hydrazine Hydrate | 0 | 0 | 0 | 0 | 0.31 |
| Ancamine ® 1922A | 2.65 | 0 | 0 | 0 | 0 |
| Ethylenediamine | 0 | 0.72 | 0.57 | 0.23 | 0 |
| Diethylenetriamine | 0 | 0 | 0 | 0.18 | 0.30 |
| Water | 61.34 | 59.56 | 59.25 | 62.64 | 56.96 |
| % Solids | 28 | 32.55 | 36.2 | 36.31 | 40 |
| pH | N/A | N/A | N/A | N/A | 7.5 |
| Mean particle size, nm | 74 | 57 | 3,134 | 123 | 73 |
| Viscosity @ 25 C., cps | 56 | 207 | 112 | 82 | 115 |
| Property |  |  |  |  |  |
| % Curl Retention | 100 | 93 | 95 | 94 | 98 |
| Style Retention | 1 | 1 | 1 | 1 | 1 |
| Adhesion to Hair | 1 | 2 | 3 | 4 | 4 |
| Feel | 1 | 1 | 1 | 2 | 1 |

As can be seen, Example 1, according to the invention, gave surprisingly good results with regard to adhesion to hair and feel, while still providing excellent results with regard to curl and style retention.

Example 6

Suntan Lotion

A suntan lotion was formulated using the polyurethane dispersion of Example 1, and having an SPF rating of 30+:

| Phase | Ingredients | Wt. % |
|---|---|---|
| A-water | Propylene Glycol | 1.00 |
|  | D. I. water | 59.75 |
|  | PUD of Example 1 | 5.00 |
|  | Polargel UV 1116 (Amcol) | 3.75 |
|  | Methylparaben and Butylparaben, and Propylparaben | 1.0 |
| B-Oil | Octyl methoxycinnamate | 5.0 |
|  | Octyl salicylate | 3.0 |
|  | Oxybenzone | 3.0 |
|  | Avobenzone | 2.0 |
|  | Isopropyl Myristate | 5.0 |
|  | Stearyl Alcohol | 2.0 |
|  | Glyceryl Stearate | 2.0 |
|  | Stearic acid | 2.0 |
|  | Polyethylene | 2.5 |
|  | Cetyl Phosphate | 1.0 |
| Total |  | 100.00 |

The sunscreen had perfect waterproofing property, applied in a smooth fashion and had good feel. Further, the sunscreen exhibited no balling effect.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for preparing an aqueous polyurethane dispersion suitable for use in personal care products, comprising:

1) preparing a prepolymer according to the formula:

$$OCN-R_2 \left[ \begin{array}{c} H \\ | \\ N \end{array} \begin{array}{c} O \\ \| \\ C \end{array} - O-R_1-O- \begin{array}{c} O \\ \| \\ C \end{array} \left( \begin{array}{c} H \\ | \\ N \end{array} - R_2 \right) \left( \begin{array}{c} H \\ | \\ N \end{array} \begin{array}{c} O \\ \| \\ C \end{array} - O-R_3-O- \begin{array}{c} O \\ \| \\ C \end{array} \begin{array}{c} H \\ | \\ N \end{array} - R_2 \right)_n \right]_m NCO$$

wherein $R_1$ represents a bivalent radical of a polycarbonate polyol, $R_2$ represents a radical of an aliphatic or cycloaliphatic polyisocyanate, $R_3$ represents a radical of a low molecular weight diol, optionally substituted with ionic groups, n is from 1 to 5, and m is >1;

by reacting:

1a) at least one polycarbonate polyol, 1b) one or more aliphatic or cycloaliphatic polyisocyanates, and 1c) at least one low molecular weight diol optionally substituted with ionic groups;

2) reacting the prepolymer with at least one monohydroxyl-functional polyalkylene oxide with a number average molecular weight equal to or less than about 3,000;
3) chain-extending the prepolymer with
   3a) at least one chain extender according to the formula:

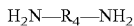
   H$_2$N—R$_4$—NH$_2$ wherein R$_4$ represents an alkylene or alkylene oxide radical not substituted with ionic or potentially ionic groups, and
   3b) optionally at least one chain extender selected from the group consisting of the sodium salt of N-(2-aminoethyl)-2-aminoethane sulfonic acid and compounds according to the formula:

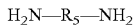
   H$_2$N—R$_5$—NH$_2$ wherein R$_5$ represents an alkylene radical substituted with ionic or potentially ionic groups,
in the presence of an organic solvent to form a polyurethane;
4) dispersing the polyurethane in water; and
5) removing the organic solvent, resulting in an aqueous polyurethane dispersion;
wherein the radical of the monohydroxyl-functional polyalkylene oxide constitutes between about 0.1 wt. % to about 5 wt. % of the polyurethane.

2. The process of claim 1, wherein the process further comprises chain terminating the prepolymer with at feast one compound according to the formula:

wherein R$_6$ is an H atom or alkylene radical optionally having a hydroxyl end and R$_7$ is alkylene radical optionally having a hydroxyl end.

3. The process of claim 2, wherein the compound for chain terminating is selected from the group consisting of methyl amine, ethylamine, propylamine, butylamine, octylamine, laurylamine, stearylamine, isononyloxy-propylamine, dimethylamine, diethylamine, dipropylamine, dibutyl amine, N-methylaminopropylamine, diethyl(methyl)aminopropylamine, morpholine, piperidine and diethanolamine, amide amines of diprimary amines and monocarboxylic acids, monoketimes of diprimary amines, primary/tertiary amines, methanol, butanol, hexanol, 2-ethylhexyl alcohol, isodecyl alcohol, aminomethylpropanol and mixtures thereof.

4. The process of claim 1, wherein the one or more polyisocyanates are selected from the group consisting of tetramethylene diisocyanate, 1,6-hexamethylene diisocyanate, dodecamethylene diisocyanate, 1,4-diisocyanatocyclohexane, 3-isocyanatomethyl-3,5,5-trimethylcyclo-hexylisocyanate (isophorone diisocyanate), 4,4'-diisocyanatodicyclohexylmethane, 4,4'-diisocyanatodicyclohexylpropane-(2,2) and mixtures thereof.

5. The process of claim 1, wherein the low molecular weight diol is selected from the group consisting of ethylene glycol, diethylene glycol, propane 1,2-diol, propane 1,3-diol, butane 1,4-diol, butylene 1,3-glycol, cyclohexane diol, 1,4-cyclohexane dimethanol, hexane 1,6-diol, bisphenol A (2,2-bis(4-hydroxyphenyl)propane), hydrogenated bisphenol A (2,2-bis(4-hydroxycyclohexyl)propane) and mixtures thereof.

6. The process of claim 1, wherein the low molecular weight diol is selected from the group consisting of dimethylol butanoic acid and dimethylol propanoic acid.

7. The process of claim 3 wherein the low molecular weight diol is selected from the group consisting of dimethylol butanoic acid and dimethylol propanoic acid.

8. The process of claim 1, wherein the second chain extender 3b) is the sodium salt of N-(2-aminoethyl)-2-aminoethane sulfonic acid.

9. The process of claim 1, wherein the monohydroxyl-functional polyalkylene oxide compound is a polyethylene oxide monol having a number average molecular weight of approximately 2220.

10. The process of claim 1, wherein n is from 1 to 3, and m is from 1 to 5.

11. The process of claim 1, wherein either R$_3$ is a radical of diethylene glycol or R$_4$ is a radical of 4,7,10-trioxa-1,13-tridecanediamine.

12. An aqueous polyurethane dispersion obtained by the process of claim 1.

13. A hair fixative comprising the aqueous polyurethane dispersion of claim 12 and water.

14. A hair fixative comprising the aqueous polyurethane dispersion of claim 12 and ethanol.

15. A suntan lotion comprising the polyurethane dispersion of claim 1.

* * * * *

UNITED STATES PATENT AND TRADEMARK OFFICE
CERTIFICATE OF CORRECTION

PATENT NO. : 7,452,525 B1  
APPLICATION NO. : 11/890979  
DATED : November 18, 2008  
INVENTOR(S) : Yuliya Berezkin et al.

It is certified that error appears in the above-identified patent and that said Letters Patent is hereby corrected as shown below:

On the title page, insert:
--Assignee: Bayer MaterialScience LLC, Pittsburgh, PA (US).--

Signed and Sealed this

Thirtieth Day of March, 2010

David J. Kappos
*Director of the United States Patent and Trademark Office*